United States Patent
Bencini et al.

(10) Patent No.: US 9,060,756 B2
(45) Date of Patent: Jun. 23, 2015

(54) BALLOON CATHETER WITH FLEXIBLE ELECTRODE ASSEMBLIES

(75) Inventors: Bob Bencini, Sunnyvale, CA (US); Frank Ingle, Palo Alto, CA (US); Joe Koblish, Sunnyvale, CA (US); Rebecca Tin, Mountain View, CA (US); Jim Mazzone, San Jose, CA (US); Byron Chun, Castro Valley, CA (US); David Lawrence, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 335 days.

(21) Appl. No.: 13/413,533

(22) Filed: Mar. 6, 2012

(65) Prior Publication Data

US 2012/0165803 A1 Jun. 28, 2012

Related U.S. Application Data

(63) Continuation of application No. 12/127,287, filed on May 27, 2008, now Pat. No. 8,128,617.

(51) Int. Cl.
*A61B 18/12* (2006.01)
*A61B 18/02* (2006.01)
*A61B 5/042* (2006.01)
*A61B 18/00* (2006.01)

(52) U.S. Cl.
CPC .............. *A61B 18/02* (2013.01); *A61B 5/0422* (2013.01); *A61B 2018/00017* (2013.01); *A61B 2018/00023* (2013.01); *A61B 2018/0022* (2013.01); *A61B 2018/0212* (2013.01); *A61B 2018/0262* (2013.01)

(58) Field of Classification Search
CPC ...................... A61B 18/02; A61B 2018/00017; A61B 2018/00023; A61B 2018/0022; A61B 2018/0212; A61B 2018/0262; A61B 5/0422
USPC ....................................... 606/20–26; 600/374
See application file for complete search history.

(56) References Cited

U.S. PATENT DOCUMENTS 3,815,604 A * 6/1974 O'Malley et al. ............... 604/22
4,643,186 A * 2/1987 Rosen et al. .................... 606/33

(Continued)

OTHER PUBLICATIONS

PentaRay-High density Mapping Catheter, Lasso 2515 Variable Circular Mapping Catheter, Biosense Webster, Johnson & Johnson, (2006) 2 pages.

(Continued)

*Primary Examiner* — Michael Peffley
*Assistant Examiner* — Daniel Fowler
(74) *Attorney, Agent, or Firm* — Seager, Tufte & Wickhem, LLC

(57) ABSTRACT

In some implementations, a method of ablating body tissue includes (a) locating an inflatable balloon portion of a cryotherapy balloon catheter at a treatment site internal to a patient's body, and inflating the inflatable balloon portion; (b) employing electrodes that are disposed on an expandable surface of the inflatable balloon portion to electrically characterize body tissue at the treatment site; (c) ablating the body tissue by supplying a cryotherapy agent to the inflatable balloon portion to cool the body tissue to a therapeutic temperature; (d) employing the electrodes to determine whether the ablating caused desired electrical changes in the body tissue; and (e) repeating (c) and (d) when it is determined that the ablating did not cause the desired electrical changes.

11 Claims, 15 Drawing Sheets

(56) References Cited

U.S. PATENT DOCUMENTS

| | | | |
|---|---|---|---|
| 5,195,970 A | 3/1993 | Gahara | |
| 5,281,213 A | 1/1994 | Milder et al. | |
| 5,344,441 A * | 9/1994 | Gronauer | 607/156 |
| 5,499,981 A * | 3/1996 | Kordis | 606/41 |
| 5,733,280 A | 3/1998 | Avitall | |
| 5,759,182 A | 6/1998 | Varney et al. | |
| 5,782,760 A * | 7/1998 | Schaer | 600/381 |
| 5,846,238 A * | 12/1998 | Jackson et al. | 606/41 |
| 5,902,299 A * | 5/1999 | Jayaraman | 606/20 |
| 6,013,055 A | 1/2000 | Bampos et al. | |
| 6,142,993 A | 11/2000 | Whayne et al. | |
| 6,270,493 B1 | 8/2001 | Lalonde et al. | |
| 6,283,959 B1 * | 9/2001 | Lalonde et al. | 606/21 |
| 6,322,559 B1 * | 11/2001 | Daulton et al. | 606/41 |
| 6,514,249 B1 * | 2/2003 | Maguire et al. | 606/41 |
| 6,551,274 B2 | 4/2003 | Heiner | |
| 6,589,238 B2 * | 7/2003 | Edwards et al. | 606/41 |
| 6,597,955 B2 * | 7/2003 | Panescu et al. | 607/122 |
| 6,640,120 B1 | 10/2003 | Swanson et al. | |
| 6,652,515 B1 | 11/2003 | Maguire et al. | |
| 6,658,279 B2 | 12/2003 | Swanson et al. | |
| 6,736,811 B2 | 5/2004 | Panescu et al. | |
| 6,970,733 B2 * | 11/2005 | Willis et al. | 600/424 |
| 2002/0065512 A1 * | 5/2002 | Fjield et al. | 606/27 |
| 2004/0087936 A1 * | 5/2004 | Stern et al. | 606/41 |
| 2004/0158237 A1 | 8/2004 | Abboud et al. | |
| 2004/0243118 A1 | 12/2004 | Ayers et al. | |
| 2005/0033136 A1 * | 2/2005 | Govari et al. | 600/374 |
| 2005/0165388 A1 * | 7/2005 | Bhola | 606/14 |
| 2006/0004353 A1 * | 1/2006 | Koyfman et al. | 606/41 |
| 2006/0069385 A1 * | 3/2006 | Lafontaine et al. | 606/21 |
| 2006/0212027 A1 * | 9/2006 | Marrouche et al. | 606/21 |
| 2006/0259023 A1 * | 11/2006 | Abboud et al. | 606/21 |
| 2006/0259029 A1 | 11/2006 | Utley et al. | |
| 2007/0083194 A1 * | 4/2007 | Kunis et al. | 606/41 |

OTHER PUBLICATIONS

Indian Pacing and Electrophysiology Journal, Pulmonary Vein Isolation with a Multielectrode Basket Catheter, (2006) 13 pages.

BSC product page, Constellation® Full contact Mapping Catheter, (2008) 3 pages.

* cited by examiner

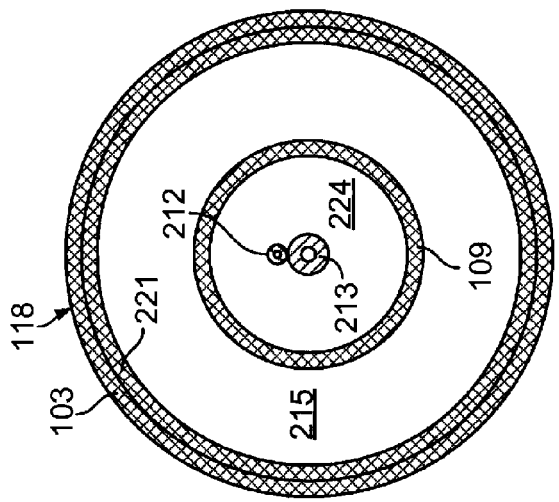
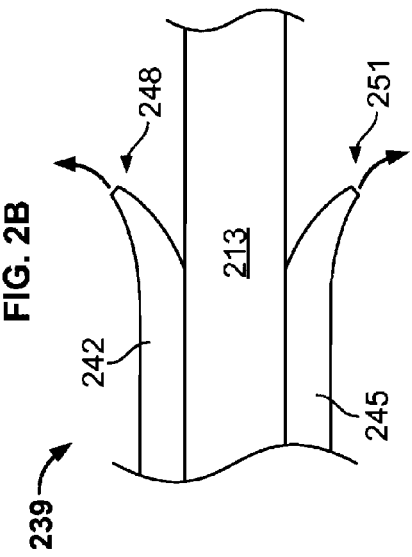
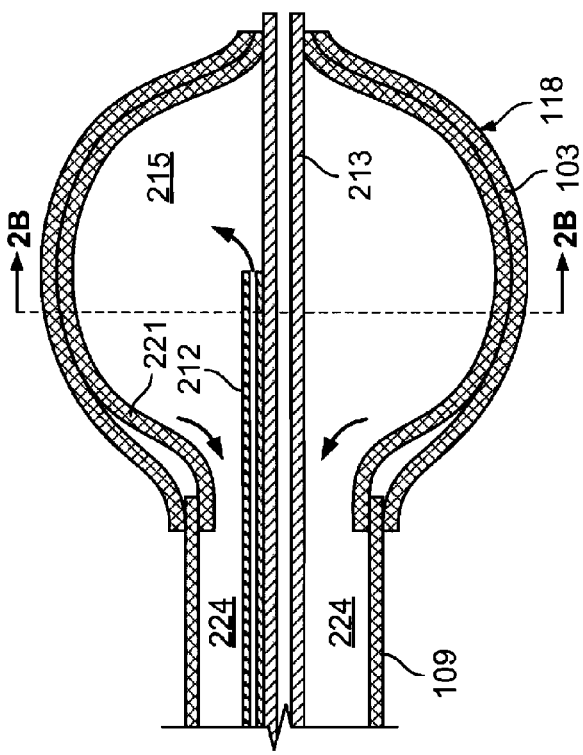
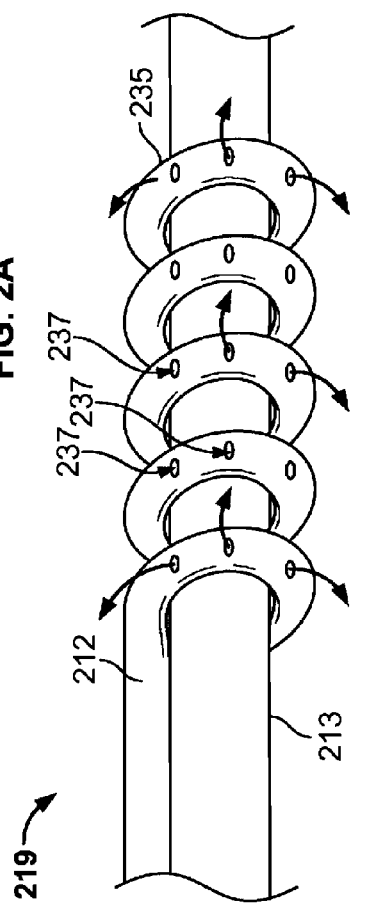

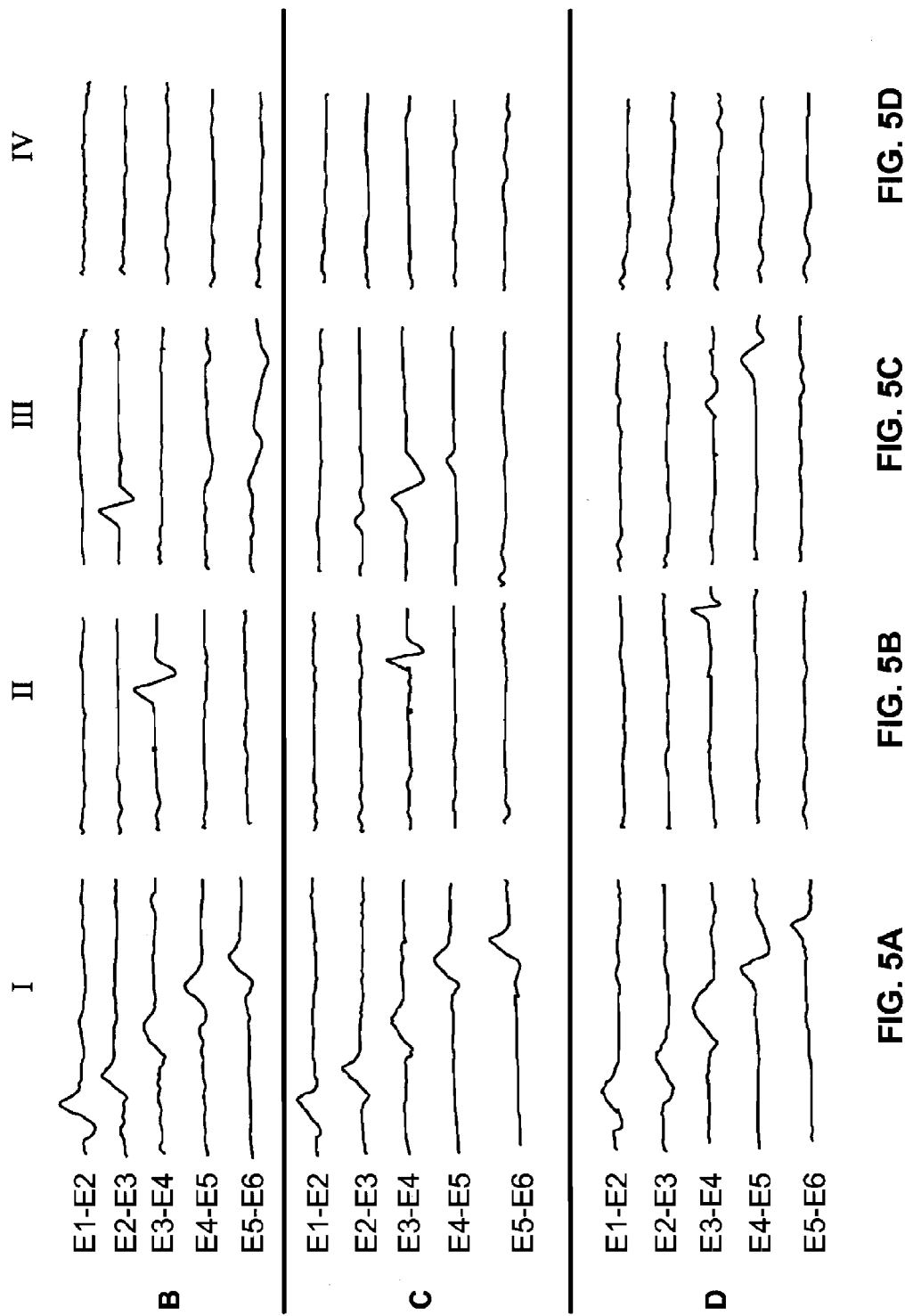

BALLOON CATHETER WITH FLEXIBLE ELECTRODE ASSEMBLIES

CROSS-REFERENCE TO RELATED APPLICATIONS

This application is a continuation of U.S. application Ser. No. 12/127,287, filed May 27, 2008, now U.S. Pat. No. 8,128,617, the entire disclosures of which are all incorporated herein by reference.

TECHNICAL FIELD

A balloon catheter for electrical mapping and cryo ablation is generally described.

BACKGROUND

A number of serious medical conditions may be treated in a minimally invasive manner with various kinds of catheters designed to reach treatment sites internal to a patient's body. One such medical condition is atrial fibrillation—a serious medical condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

One method of ablating tissue of the heart and pulmonary veins to control atrial fibrillation includes delivering radiofrequency (RF) energy to the tissue to be ablated. In particular, high frequency energy can be employed, for example, to cause ionic agitation and frictional heat in targeted tissue, causing permanent damage to the tissue. Once damaged, the tissue may no longer propagate or source electrical signals, and the fibrillation may be treated or reduced. The RF energy can be delivered by an RF catheter having an RF source at a distal treatment end that is positioned at a treatment site inside a patient during a treatment procedure.

Another method of ablating tissue of the heart and pulmonary veins to control atrial fibrillation is through cryotherapy, or the extreme cooling of body tissue. Cryotherapy may also cause permanent alteration to treated tissue, preventing the treated tissue from propagating or sourcing electrical signals, thereby reducing or eliminating atrial fibrillation. Cryotherapy may be delivered to appropriate treatment sites inside a patient's heart and circulatory system by a cryotherapy catheter. A cryotherapy catheter generally includes a treatment member at its distal end, such as an expandable balloon having a cooling chamber inside. A cryotherapy agent may be provided by a source external to the patient at the proximal end of the cryotherapy catheter and delivered distally through a lumen in an elongate member to the cooling chamber where it is released. Release of the cryotherapy agent into the chamber cools the chamber, the balloon's outer surface, and tissue that is in contact with the outer surface, to perform ablation. The cryotherapy agent may be exhausted proximally through an exhaust lumen in the elongate member to a reservoir external to the patient.

In addition to facilitating permanent tissue alteration, cryotherapy facilitates temporary electrical inactivation of tissue in a manner that enables a physician to test the likely results of ablation through a reversible process. Such a process is commonly referred to as cryomapping, and generally involves cooling tissue to near freezing (e.g., to 0° C.) but well above a temperature at which the tissue would be ablated (e.g., −20° C.).

It may be advantageous to map the electrical activity of a pulmonary vein (or other treatment site) prior to permanent ablation by either RF or cryotherapy, in order to pinpoint appropriate ablation target sites. Some apparent target sites may not actually contribute to abnormal electrical activity, and treating such sites may not be desirable. Treating other target sites may affect healthy tissue in undesirable ways (e.g., creating conduction blocks). Precisely mapping the electrical activity in a target treatment region can help focus the treatment and confirm its efficacy and safety.

Various specialized mapping catheters may be employed to electrically map tissue, such as a circular catheter or a multi-electrode basket catheter. Such mapping catheters can be positioned at possible treatment sites inside a patient, and electrodes at those sites can provide signals to a processing system external to the patient that can process the signals and provide physicians with information to subsequently position a separate RF or cryotherapy catheter and deliver with that separate catheter appropriately targeted ablation energy.

SUMMARY

In some implementations, an inflatable distal balloon portion of a cryotherapy balloon catheter includes electrodes on its expandable surface that can enable a single balloon catheter to be used to both electrically map a potential treatment site inside a patient's body and provide cryotherapy to the treatment site. In operation, the distal balloon portion can be located at a treatment site internal to a patient's body and inflated; the electrodes can be employed to electrically characterize body tissue at the treatment site; when the electrical characterization indicates that ablation is appropriate for the body tissue at the treatment site, cryotherapy can be delivered to the treatment site (e.g., a cryogenic agent can be delivered to the distal balloon portion); and following cryotherapy delivery, the electrodes can be employed to again characterize the body tissue at the treatment site to confirm that the electrical properties of the body tissue were altered by the cryotherapy in a desirable manner. Throughout the electrical characterization and cryotherapy treatment, the distal balloon portion may remain at a fixed location. That is, electrical characterization (at two or more different times), and cryotherapy delivery, can be performed without moving the cryotherapy catheter, once it is initially positioned.

In some implementations, the distal balloon portion includes more than one inflatable balloons, such that at least one balloon forms a safety chamber to protect body tissue in the event that one balloon ruptures or is otherwise compromised. In multi-balloon implementations, electrodes can be disposed on a balloon other than the outermost balloon. For example, electrodes code be disposed on an inner safety balloon, and a material for the outer balloon could be selected such that good electrical contact is provided between electrodes on the safety balloon and body tissue adjacent to the electrodes and in contact to the external surface of an outer balloon.

In some implementations, the body tissue can be electrically characterized during the cryotherapy treatment. Moreover, the cryotherapy treatment may be broken into two phases: a first mapping phase, during which body tissue is only temporarily altered (e.g., by cooling the body tissue to a first temperature) to confirm the likelihood that permanent treatment will be efficacious; and a second treatment phase, during which the body tissue can be permanently altered (e.g., by cooling the body tissue to a second temperature that is lower than the first temperature).

In some implementations, some electrodes can also be used to stimulate body tissue (e.g., during the first phase) and other electrodes can be used to detect stimulation signals. For example, by providing an electrical stimulus signal at one electrode, and detecting the signal at one or more other electrodes, body tissue may be electrically characterized in the absence of electrical signals generated by the body tissue itself. Such stimulus-based tissue characterization may be advantageous at various points of therapy, including before, during or after cryotherapy is delivered, and the characterization may be useful in determining whether particular regions of body tissue are good candidates for cryotherapy, or whether previously administered cryotherapy has caused its intended effect.

The details of one or more implementations are set forth in the accompanying drawings and the description below. Other features, objects, and advantages will be apparent from the description and drawings, and from the claims.

BRIEF DESCRIPTION OF DRAWINGS

FIGS. 2A-2D illustrate additional details of internal structures of the inflatable balloon portion that is shown in FIG. 1.

FIGS. 5A-5D illustrate example electrical signals that can be obtained from the electrodes shown in FIGS. 3 and 4 to electrically characterize body tissue that is contact with the inflatable balloon of FIG. 1.

Like reference symbols in the various drawings indicate like elements.

DETAILED DESCRIPTION

Figure 1:
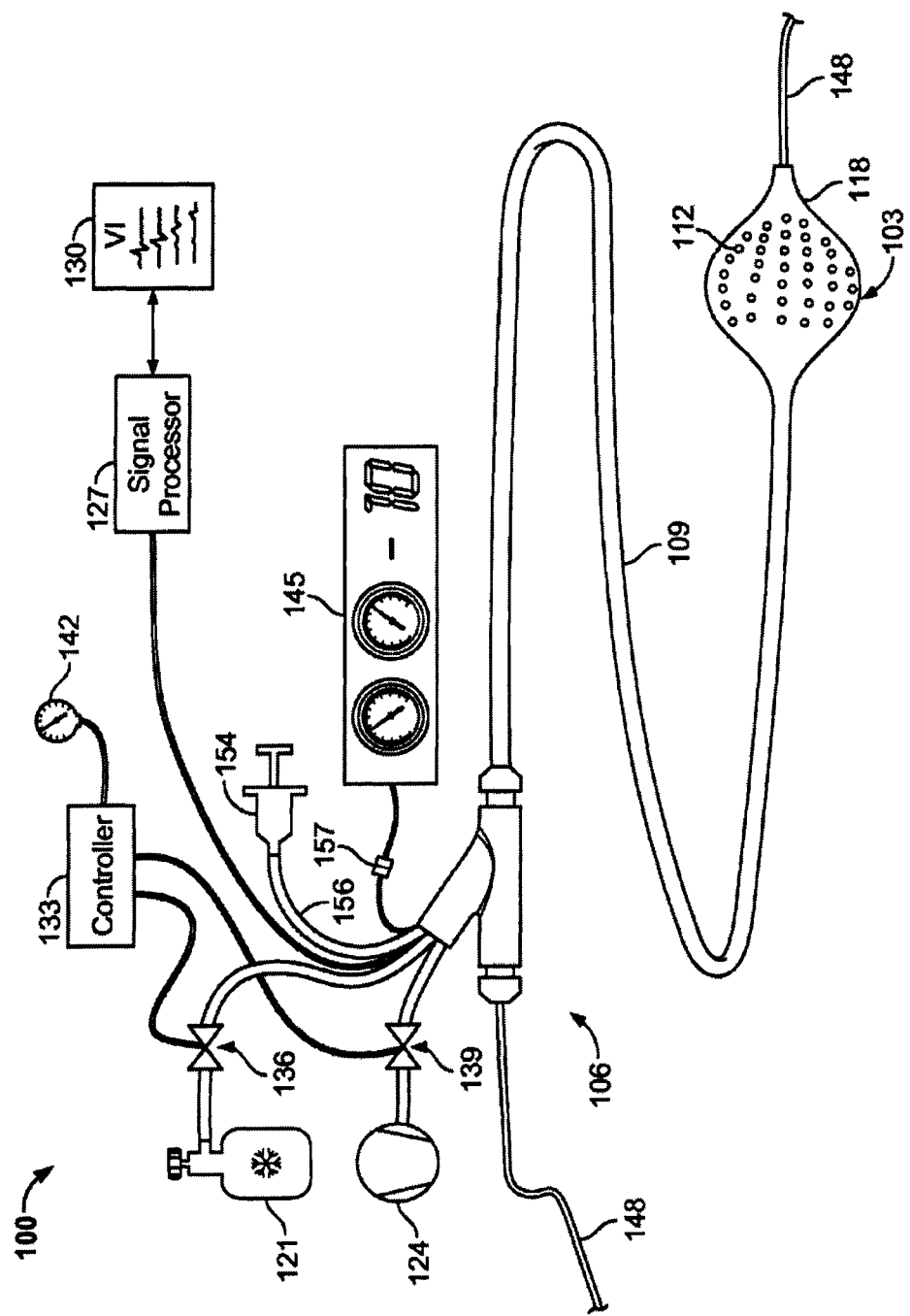
FIG. 1 is a diagram of an example cryotherapy catheter having an inflatable balloon portion that can be employed to electrically characterize body tissue and deliver cryotherapy to the body tissue.

FIG. 1 is a diagram of an example cryotherapy catheter 100 that can be employed to electrically characterize body tissue and deliver cryotherapy to the body tissue. As shown in one implementation, the cryotherapy catheter 100 includes a distal inflatable balloon portion 103 that can be routed to a treatment site inside a patient to electrically characterize and deliver cryotherapy to that treatment site; a proximal end 106 that remains outside a patient during treatment and facilitates connection of various equipment to the cryotherapy catheter; and an elongate member 109 that couples the proximal-end equipment to the distal inflatable balloon portion.

Figure 15:
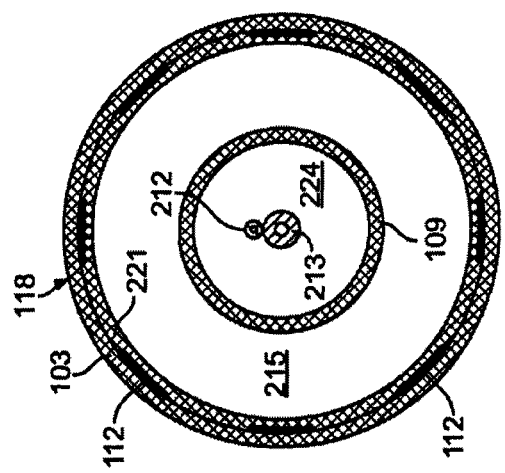
FIG. 15 is a cross-section of an example cryotherapy catheter having inner and outer balloons.

The distal inflatable balloon portion 103 includes a number of electrodes 112 on its expandable surface 118 that can be employed to electrically characterize tissue that is contact with the electrodes 112 at the treatment site. In particular, for example, the electrodes can be configured to support a detailed intracardiac electrophysiology study. Other types of electrodes or sensors can also be included on or near the surface 118 of the balloon 103, such as, for example, thermal or pressure sensors. As is described in more detail below, the distal inflatable balloon portion 103 can include more than one balloon. For example, a second safety balloon can be included inside an outer balloon to isolate body fluids from the inside of the balloon 103 portion, and to isolate therapy agents inside the balloon portion 103 form body tissue, in the event that the integrity of one of the balloons is compromised. In such multi-balloon implementations, the electrodes 112 can be disposed on an inner balloon 221, as shown in FIG. 15, and the outer balloon can be constructed to facilitate appropriate electrical contact between the electrodes and body tissue, through the outer balloon.

The catheter's elongate member 109 has multiple internal lumens (not shown in FIG. 1). The lumens allow cryogenic fluid to be delivered distally from an external cryogenic fluid source 121 to an internal chamber of the balloon 103. In addition, the internal lumens of the elongate member 109 allow exhaust resulting from delivery of cryogenic fluid to the internal chamber of the balloon 103 to be delivered proximally from the internal chamber to an external exhaust pump 124. During operation, there may be continuous circulation within the elongate member 109 of cryogenic fluid distally and exhaust proximally. The elongate member 109 also includes conductors (not shown) that carry electrical signals from the electrodes 112 to a signal processor 127 at the proximal end of the catheter 100.

The signal processor 127 can process the electrical signals to electrically characterize body tissue that is in contact with the electrodes. In particular, the signal processor 127, in some implementations, generates visual displays, such as isochronal or isopotential maps of the tissue, which a physician may use to identify aberrant electrical pathways at locations in the body tissue that may be candidates for ablation. The visual displays may be provided in a user interface 130 (e.g., a flat panel display, or other suitable output device). Example displays are described further below, with reference to FIGS. 5A-5D.

The signal processor 127 can include circuitry for receiving biopotential signals (e.g., differential amplifiers or other amplifiers that sense biopotential signals and amplify them to levels that can be used in further processing) and processing the signals in a manner that permits their subsequent analysis, for example by a medical professional delivering or considering delivering cryotherapy to a patient. The signal processor 127 can also include circuitry for generating stimulation signals that may be routed to one or more of the electrodes 112. For example, in some implementations, it is advantageous to stimulate portions of tissue with one or more electrodes and measure the electrical effect of such stimulation with one or more other adjacent or nearby electrodes. In this manner, aberrant electrical pathways may be identified, even if a source of electrical impulses that would travel over the aberrant electrical pathways is not active when the tissue is analyzed.

In some implementations, the signal processor 127 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for processing biopotential signals and displaying a graphical representation of the signals in a user interface. In some implementations, the signal processor 127 includes a general purpose microprocessor and/or a specialized microprocessor (e.g., a digital signal processor, or DSP, which may be optimized for processing graphical or a biometric information) that executes instructions to receive, analyze and display information associated with the received biopotential signals. In such implementations, the signal processor 127 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the signal processor 127 can take any suitable form.

A controller 133 at the proximal end can regulate flow of cryogenic fluid to the internal chamber of the balloon 103 and flow of exhaust from the balloon 103. In particular, for example, the controller 133 can, in one implementation as shown, regulate a valve 136 that controls flow of the cryogenic fluid from the cryogenic fluid source 121. The cryogenic fluid source 121 may be, for example, a pressured flask of cryogenic fluid. In other implementations (not shown), the controller controls a pump and/or pump valve combination to deliver cryogenic fluid to the internal chamber of the balloon. Similarly, the controller 133 can regulate a valve 139 and/or external exhaust pump 124 to regulate flow of exhaust from the internal chamber of the balloon.

By controlling both the rate at which cryogenic fluid is delivered to the balloon 103 and the rate at which exhaust is extracted from the balloon 103, the controller 133 can develop and maintain a pressure inside the balloon 103 at a number of different values. For example, when cryogenic fluid is delivered at a very low rate to the balloon 103, and exhaust is similarly extracted at a very low rate, the balloon 103 may be inflated, but very little heat (if any) may be extracted from the balloon 103 or from body tissue that is in contact with the balloon's surface 118. As another example, when cryogenic fluid is delivered at a higher rate, heat can be extracted from the balloon 103 and from body tissue that is in contact with the balloon 103. Varying the rate at which exhaust is extracted from the balloon 103 relative to the rate at which the cryogenic fluid is supplied to the balloon can control the pressure inside the balloon 103. In particular, for example, for a given rate at which the cryogenic fluid is supplied to the balloon, a greater rate at which exhaust is extracted from the balloon 103 will generally result in lower pressure inside the balloon, and a lower rate at which exhaust is extracted from the balloon 103 will generally result in greater pressure inside the balloon.

To precisely control pressures or flow rates, the controller 133 may employ either or both of open- or closed-loop control systems. For example, in some implementations, a rate at which cryogenic fluid (e.g., the position of the valve 136) may be controlled with an open-loop control system, and a rate at which exhaust is extracted from the balloon 103 (e.g., the position of the valve 139, or the pressure exerted by the pump 124) may be controlled with a closed-loop control system. In other implementations, both rates may be controlled by closed-loop control systems. In a closed-loop control system, some feedback mechanism is provided. For example, to control the rate at which exhaust is extracted from the balloon 103, the controller 133 may employ an exhaust flow sensor device (not shown), a pressure sensor (not shown) inside the balloon 103 or elsewhere in the system, or another feedback sensor. In addition, the controller 133 may employ an ambient pressure gauge 142 in one of its control loops (e.g., to measure atmospheric pressure at the proximal end 106 of the cryotherapy catheter that remains outside the patient).

In some implementations, as mentioned above, pressure inside the balloon 103 may be primarily controlled by controlling the rate at which exhaust is extracted from the balloon 103 (given the significant difference between the large volume of gas resulting from a corresponding smaller volume of cryogenic fluid being released into the balloon 103). Temperature inside the balloon 103, on the other hand, may depend on control of both the flow of cryogenic fluid and the flow of exhaust.

The controller 133 itself can take many different forms. In some implementations, the controller 133 is a dedicated electrical circuit employing various sensors, logic elements and actuators. In other implementations, the controller 133 is a computer-based system that includes a programmable element, such as a microcontroller or microprocessor, which can execute program instructions stored in a corresponding memory or memories. Such a computer-based system can take many forms, include many input and output devices (e.g., the user interface 130 and other common input and output devices associated with a computing system, such as keyboards, point devices, touch screens, discrete switches and controls, printers, network connections, indicator lights, etc.) and may be integrated with other system functions, such as monitoring equipment 145 (described in more detail below), a computer network, other devices that are typically employed during a cryotherapy procedure, etc. For example, a single computer-based system may include a processor that executes instructions to provide the controller function, display imaging information associated with a cryotherapy procedure (e.g., from an imaging device); display pressure, temperature and time information (e.g., elapsed time since a given phase of treatment was started); and serve as an overall interface to the cryotherapy catheter. In general, various types of controllers are possible and contemplated, and any suitable controller 133 can be employed. Moreover, in some implementations, the controller 133 and the signal processor 127 may be part of a single computer-based system, and both control and signal processing functions may be provided, at least in part, by the execution of program instructions in a single computer-based system.

The catheter 100 shown in FIG. 1 is an over-the-wire type catheter. Such a catheter 100 uses a guidewire 148, extending from the distal end of the catheter 100. In some implementations, the guidewire 148 may be pre-positioned inside a patient's body; once the guidewire 148 is properly positioned, the balloon 103 (in a deflated state) and the elongate member 109 can be routed over the guidewire 148 to a treatment site. In some implementations, the guidewire 148 and balloon portion 103 of the catheter 100 may be advanced together to a treatment site inside a patient's body, with the guidewire portion 148 leading the balloon 103 by some distance (e.g., several inches). When the guidewire portion 148 reaches the treatment site, the balloon 103 may then be advanced over the guidewire 148 until it also reaches the treatment site. Other implementations are contemplated, such as steerable catheters that do not employ a guidewire. Moreover, some implementations include an introducer sheath that can function similar to a guidewire, and in particular, that can be initially advanced to a target site, after which other catheter portions can be advanced through the introducer sheath.

The catheter 100 can include a manipulator (not shown), by which a medical practitioner may navigate the guidewire 148 and/or balloon 103 through a patient's body to a treatment site. In some implementations, release of cryogenic fluid into the cooling chamber may inflate the balloon 103 to a shape similar to that shown in FIG. 1. In other implementations, a pressure source 154 may be used to inflate the balloon 103 through an inflation lumen 156, independently of the release of cryogenic fluid into the internal chamber of the balloon 103. The pressure source 154 may also be used to inflate an anchor member on the end of the guidewire 148 (not shown).

The catheter 100 includes a connector 157 for connecting monitoring equipment 145. The monitoring equipment may be used, for example, to monitor temperature or pressure at the distal end of the catheter 100. As indicated above, the monitoring equipment 145 may be integrated in a single system that also provides the controller 133 and signal processor 127.

To aid in positioning the treatment member 103 of the catheter 100 inside a patient's body, various marker bands (not shown) can also be disposed at the distal and proximal ends of the catheter 100. The marker bands may be radioopaque when the catheter is viewed by x-ray or other imaging techniques.

Other variations in the catheter 100 are contemplated. For example, the monitoring equipment 145 is shown separately in FIG. 1, but in some implementations, displays associated with the monitoring equipment are included in the user interface 130. The controller 133 is depicted as controlling valves 136 and 139 to regulate the flow of cryogenic fluid to the balloon 103 and channeling exhaust from the balloon 103, but other control schemes (e.g., other valves or pumps) can also be employed. Electrodes can be arranged in ways other than shown in FIG. 1. A guidewire may be arranged differently than shown, and may be separately controlled from the balloon portion of the catheter. Moreover, in some implementations, a guidewire may not be used.

FIGS. 2A-2D illustrate additional details of internal structures of the balloon 103 that can deliver cryotherapy. FIG. 2A shows a longitudinal cross-section of the example cryotherapy balloon 103 and an example elongate member 109 through which cryogenic fluid and exhaust may be cycled to and from an internal chamber 215 of the cryotherapy balloon 103. As shown in FIG. 2A, cryogenic fluid may be delivered from an external source (e.g., 121 in FIG. 1) to a cooling chamber 215 internal to the balloon 103 via a coolant delivery lumen 212. In some implementations, an exhaust lumen 224 may be defined generally by the outer layer of the elongate shaft 109, as shown. In other implementations, the catheter may include one or more dedicated exhaust lumen structures (not shown) that are defined independently of the elongate member 109.

The coolant may be released into the cooling chamber 215 from an opening at the end of the delivery lumen 212, or the coolant may be released through a cryotherapy device 219 or 239 (see FIGS. 2C and 2D) disposed at the end of the delivery lumen 212. In some implementations, the cooling device 219 includes a coiled extension 235 having a number of apertures 237 from which pressurized liquid coolant can escape and change state to a gas.

The cooling device can take other forms. For example, as shown in FIG. 2D, a cooling device 239 may include multiple coolant delivery lumens 242 and 245, each with a corresponding aperture 248 and 251 through which coolant can be released. Such a design can permit coolant to be released in a directional manner. For example, if coolant is only delivered through the lumen 242, and not through the lumen 245, cooling can be concentrated in the upper half of the balloon 103. Two separate cooling lumens are shown, but more than two can be provided. For example, with four coolant lumens, cooling within one or more specific circumferential quadrants may be possible, depending on which lumens carry the coolant. In devices having multiple cooling lumens, the reader will appreciate that the controller 133 could control multiple cryogenic fluid supply valves to precisely control regions of cooling.

In some implementations, the coolant undergoes a phase change within the cooling chamber 215, cooling the chamber 215 via the Joule-Thomson effect, as well as cooling the external surface 118 of the outermost balloon 103 and a patient's body tissue that is adjacent to the external surface 118 of the outer balloon. The cryogenic fluid, or gas if the fluid has undergone a phase change, is then exhausted through the exhaust lumen 224 to a reservoir, pump or vacuum source external to the catheter (e.g., 124 in FIG. 1). In some implementations, there is a continuous cycle of cryogenic fluid to the cooling chamber 215 via the delivery lumen 212 and exhaust from the cooling chamber 215 via the exhaust lumen 224.

The coolant that is cycled into the chamber 215 is one that will provide the appropriate heat transfer characteristics consistent with the goals of treatment. In some implementations, liquid N2O may be used as a cryogenic coolant. When liquid N2O is used, it may be transported to the cooling chamber 215 in the liquid phase where it changes to a gas at the end of the coolant delivery lumen 212, or from the apertures 237 of a cooling device 219. Other implementations may use Freon, Argon gas, and CO2 gas, or other agents as coolants.

In some implementations, as shown, a second balloon 221 is provided within the outer balloon 103 to isolate the cryogenic fluid within the cooling chamber 215. In these implementations, the outer balloon 103 forms a safety chamber that prevents coolant from escaping if the cooling chamber 215 balloon 221 bursts. A separate vacuum lumen (not shown) may be provided to evacuate any gas or liquid that escapes from the internal cooling chamber 215; alternatively, any gas or liquid that breaches the second balloon 221 but not the second balloon 103 may still be exhausted through the exhaust lumen 224. In operation, the outer and inner balloons 103 and 221 may expand and deflate together. In some implementations, release of coolant inflates the balloons 103 and 221. In some implementations, the balloons 103 or 221 are first inflated by the injection of an inflation fluid or gas (e.g., a saline solution or an inert gas), after which the coolant may be introduced to the cooling chamber 115.

FIG. 2B shows a radial cross-section along the line A-A that is shown in FIG. 2A. In over the-wire implementations, the cryotherapy catheter 100 includes a guidewire lumen 213, which allows the balloon 103 to be routed to a treatment site inside a patient over a pre-positioned guidewire. As shown in FIG. 2B, the coolant delivery lumen 212 is adjacent to the guidewire lumen 213, and the guidewire lumen 213 is shown to be substantially coaxial with the exhaust lumen 224, which corresponds to the overall shaft (e.g., elongate member 109) of the catheter. In some implementations, lumens may have other arrangements, and more or fewer lumens may be included in the catheter. For example, the coolant delivery lumen 212 may be disposed coaxially around the guidewire lumen 213; the coolant delivery lumen 212 may be differently disposed within the chamber 215, such that it is not coaxial with respect to the guidewire lumen 213 or other lumens; multiple, separately controllable coolant delivery lumens may be provided; the guidewire lumen 213 may be omitted in a steerable catheter design; lumens for steering members may be provided; one or more vacuum lumens may be included; one or more exhaust lumens may be included that are independent of the outer layer of the catheter shaft 109; additional lumens may be provided for inflating or deflating the balloons 103 or 221 or for inflating or deflating other balloons not shown in FIG. 2A; additional lumens may be provided to control an anchor member that may be disposed on a guidewire near the distal portion of the balloon 103; or additional lumens may be provided to carry wires or other conductors for electrodes on the surface 118 of the balloon 103 (electrodes not shown in FIGS. 2A-2D).

In some implementations, the balloon 103, and a corresponding internal cooling chamber, if present (e.g., balloon 221, shown in FIG. 2A), may be formed from a polymer including, but not limited to, polyolefin copolymer, polyester, polyethylene teraphthalate, polyethylene, poly ether-block-amide, polyamide, polyimide, nylon, latex, or urethane. For example, certain implementations of the balloon 103 comprise PEBAX® 7033 material (70D poly ether amide block). The balloon 103 may be made by blow-molding a polymer extrusion into the desired shape, or cast onto or inside of a form. In some embodiments, the balloon 103 may be constructed to expand to a desired shape when pressurized without elastically deforming substantially beyond the desired shape. In some implementations, the molding process may be modified in order to create longitudinal splines, or thicker ridges to accommodate splines or wires, or both (splines are described in more detail below). For example, a mandrel used in the molding process could be modified to have ridges corresponding to desired splines or ridges in the balloon.

A number of ancillary processes may be used to affect the material properties of the balloon 103. For example, the polymer extrusion may be exposed to gamma or electron beam (e-beam) radiation which alters the polymer infrastructure to provide uniform expansion during blow molding and additional burst strength when in use. In addition, the molded balloon 103 may be exposed to a low temperature plasma field and oxidizing atmosphere, which alters the surface properties to provide enhanced adhesion characteristics. Those skilled in the art will recognize that other materials and manufacturing processes may be used to provide a balloon portion 103 suitable for use with the catheter.

Figure 3:
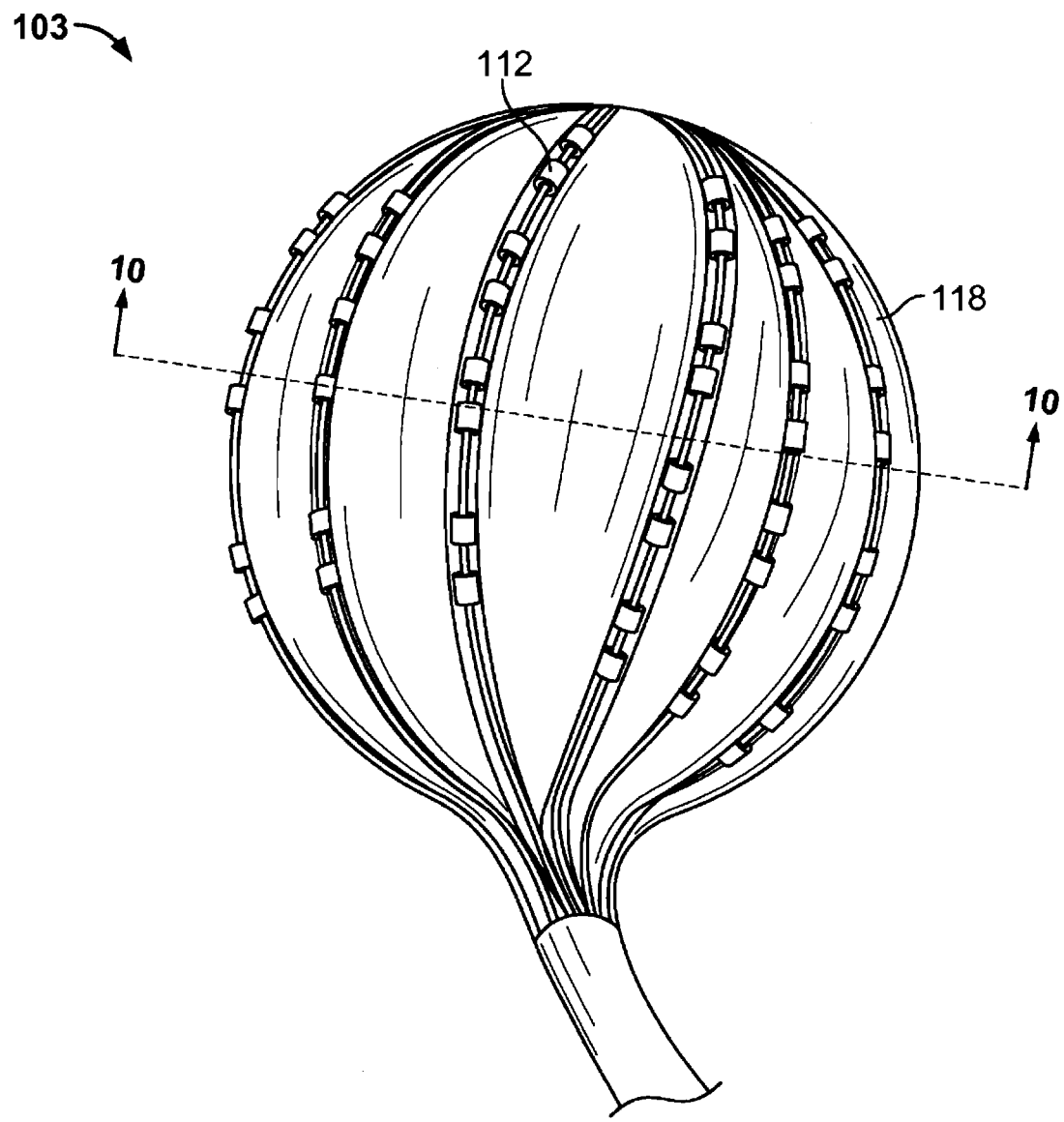
FIG. 3 illustrates example details of the electrodes that can be disposed on the surface of the inflatable balloon of FIG. 1.

FIG. 3 is a perspective view of the cryotherapy balloon 103, illustrating additional example details of the electrodes 112 disposed on its surface 118. In some implementations, as depicted in FIG. 3, the electrodes 112 are disposed in regular array. More particularly, for example, the electrodes can be disposed at regular intervals along longitudinal lines along the surface of the balloon, such that when the balloon is inflated and in contact with body tissue, biopotential signals can be measured at points along a regularly spaced grid. In other implementations, the electrodes are distributed in a different manner. For example, as described in greater detail with reference to FIGS. 6A and 6B, the electrodes may be staggered and disposed on only a portion of the balloon 103.

In some implementations, the electrodes are integral to the balloon surface (e.g., molded into the balloon material itself). In other implementations, the electrodes may be attached to the surface of the balloon by various methods. In still other implementations, as described in greater detail below, the electrodes may be mounted to other structures, such as splines or ribbons that are adjacent to or attached to the balloon.

Figure 4:
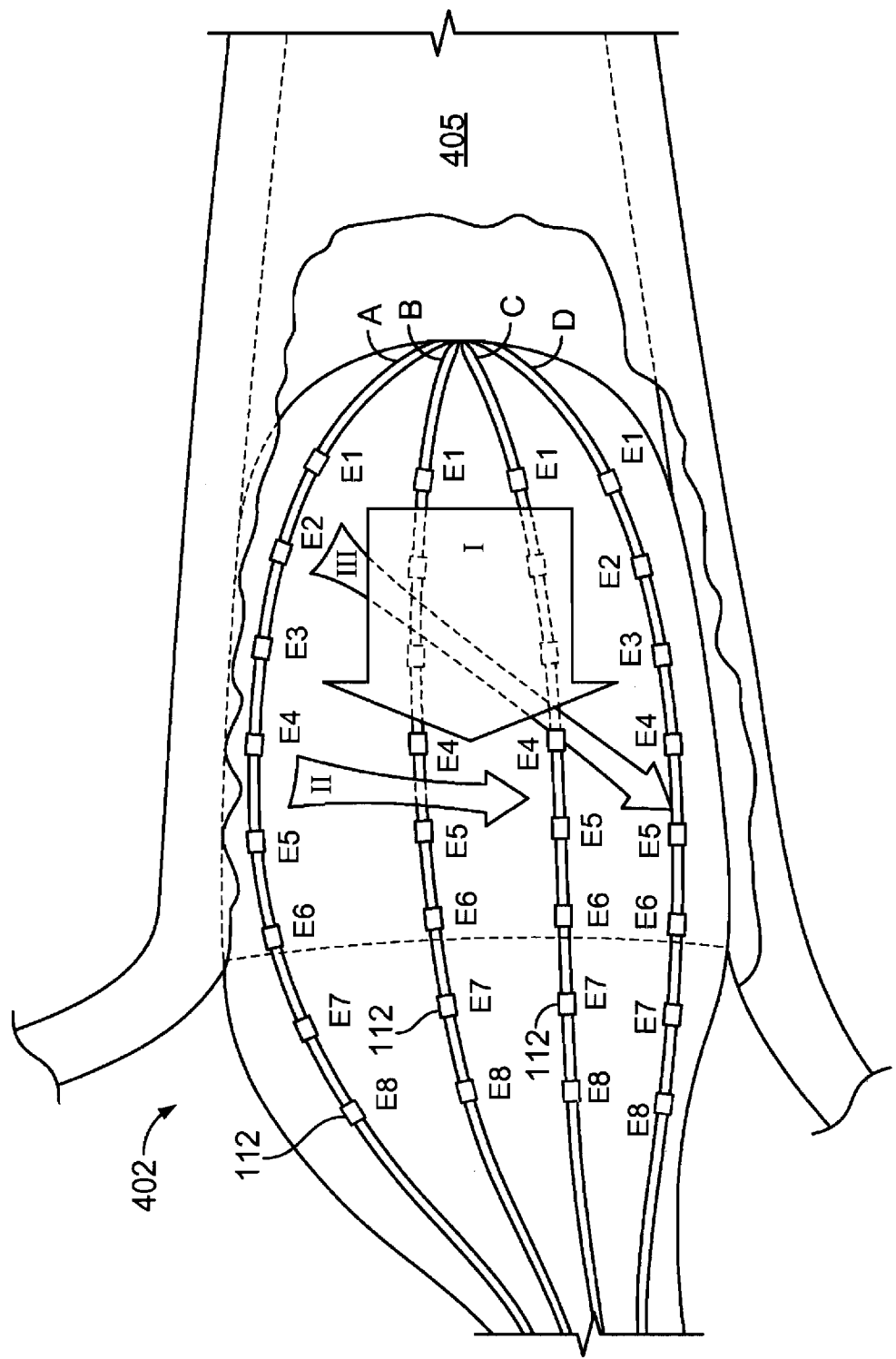
FIG. 4 illustrates additional example details of the electrodes that are shown in FIG. 3.

FIG. 4 illustrates additional detail of the example electrodes 112 shown in FIG. 3. In this particular example, the electrodes are disposed on multiple splines, four of which are visible, and the splines are shown at an example treatment site inside a body cavity (e.g., the ostium 402 of a pulmonary vein 405 (shown in a partial cut-away view) inside a patient's heart). For purposes of explanation, the visible splines in FIG. 4 are labeled as A, B, C and D. Each spline is shown with eight electrodes 112, which are labeled as E1-E8. The arrangement depicted is merely exemplary (e.g., in which the splines are disposed longitudinally, relative to an axis that is common to the balloon 103 and elongate member 109), and other arrangements are contemplated. For example, a catheter may include a greater or fewer number of splines (e.g., four, six, eight, ten, etc.), and each spline may have a greater or fewer number of electrodes (e.g., four, five, eight, ten, etc.).

In some implementations, differential biopotential measurements are made between pairs of adjacent electrodes on any given spline. For example, one biopotential measurement can be made across electrodes E1 and E2 on spline D; a second biopotential measurement can be made across electrodes E2 and E3; a third measurement can be made across E3 and E4, and so on. By measuring biopotentials at various pairs of electrodes over time, an electrical "map" can be created to characterize and visually depict electrical activity in tissue that is in contact with the electrodes. In other implementations, electrodes can be employed in a unipolar, or modified differential mode, in which the potential from one or more electrodes is measured relative to single common electrode (e.g., a reference electrode disposed at some location on the catheter), or relative to an average value of some or all of the other electrodes. Several examples of how the electrodes can be used to characterize electrical activity are now described with continued reference to FIG. 4 and reference to FIG. 5.

In a first example, the electrodes are employed to detect a electrical signal ("electrical signal I") that propagates parallel to the length of the pulmonary vein (and along the longitudinal axis of the splines). As depicted in FIG. 5A, the electrical signal I is initially detected by electrodes E1 and E2 on splines B, C and D at nearly the same time. Over time (represented by the x-axis in FIGS. 5A-5D), the signal is detected subsequently at electrode pair E2-E3, then pair E3-E4, then at pair E4-E5, then at pair E5-E6. Again the signal is seen on corresponding pairs of splines B, C and D at substantially the same time, given that the signal is propagating parallel to the splines.

Information about electrical signals, such as that shown in FIGS. 5A-5D, can be displayed in the user interface 130 (e.g., a set of graphical displays on a flat panel display that are configured to provide graphical and other information for electrically characterizing body tissue). In some implementations, the electrical characterization information includes static screen captures of biopotential information at different points in a particular region of body tissue (e.g., points corresponding to electrodes on the inflatable balloon 103); the information can include animations illustrating time-varying biopotential information; the information can include color-coded isochronal or isopotential information; the information can incorporate other information previously obtained (e.g., previous electrical physiology studies of patient, previously obtained x-rays or MRI images, etc.), or contemporaneously obtained with other equipment (e.g., imaging equipment that is employed during the cryotherapy procedure); etc.

FIG. 5B illustrates another example electrical signal ("electrical signal II") that propagates along the circumference of the pulmonary vein and in a direction transverse to the splines. In this example, the electrical signal is first detected by electrode pair E3-E4 on spline B, then on electrode pair E3-E4 on spline C, then on electrode pair E3-E4 on spline D. As depicted in FIG. 5B, the delay between when the signal is respectively detected on splines B, C and D indicates that the electrical signal I is traveling circumferentially, rather than over a large area of the length the pulmonary vein, as in the case with the electrical signal I depicted in FIG. 5A.

FIG. 5C illustrates another example electrical signal ("electrical signal III") that propagates both circumferentially and longitudinally along the pulmonary vein. In this example, the electrical signal is first detected primarily by electrode pair E2-E3 of spline B and secondarily by electrode pair E2-E3 of spline C. Next, it is detected by the electrode pair E3-E4 of spline C, followed by electrode pair E4-E5 of spline C. Finally, the signal is detected by electrode pair E4-E5 of spline D.

A final example is provided in FIG. 5D in which no substantial electrical activity is detected at any electrode pairs on any of the splines depicted. This example may correspond to a pulmonary vein that has been treated (e.g., ablated) to eliminate aberrant electrical signal sources or pathways that may be giving rise to or contributing to an adverse condition, such as atrial fibrillation. This example may also correspond to normal tissue that does not require treatment.

Disposing electrodes directly on the surface of a treatment member, such as a cryotherapy balloon, may give rise to significant advantages. In particular, for example, the electrodes can facilitate mapping and characterization of electrical signals, as depicted in FIGS. 5A-D, before, during and after treatment—without requiring the balloon 103 to be moved, and without requiring a separate catheter to be employed for mapping. Procedures involving a single catheter that can both map and provide cryotherapy treatment can reduce risks to the patient associated with switching catheters mid-procedure or employing multiple catheters during the procedure. In addition, electrical characterization can be very accurate, since the electrodes may not move much (if at all) during a cryotherapy procedure. Accordingly, the electrical characterization before, during and after the procedure can accurately relate to the same region of tissue. Moreover, a patient can benefit from a catheter that permits electrical characterization of tissue during cryomapping, in which the tissue is only temporally treated. If the electrical characterization indicates that desirable electrical changes result from cryomapping, the cryotherapy can be continued at colder temperatures and/or for longer times (without moving the balloon 103). Conversely, if electrical characterization indicates that desirable electrical changes do not result from cryomapping at a particular region of tissue, permanent treatment of that region can be avoided, limiting the tissue that is permanently remodeled to only that tissue which provides aberrant electrical pathways or sources or electrical energy. Directional therapy, which may be possible with individual directional coolant lumens, such as lumens 242 and 245 shown in FIG. 2D, may also be possible with cryotherapy balloon catheters having electrodes disposed on the expandable surface of the balloon, and the direction in which cryotherapy is directed can be determined based on which electrodes pick up abnormal electrical signals.

Figure 6A:
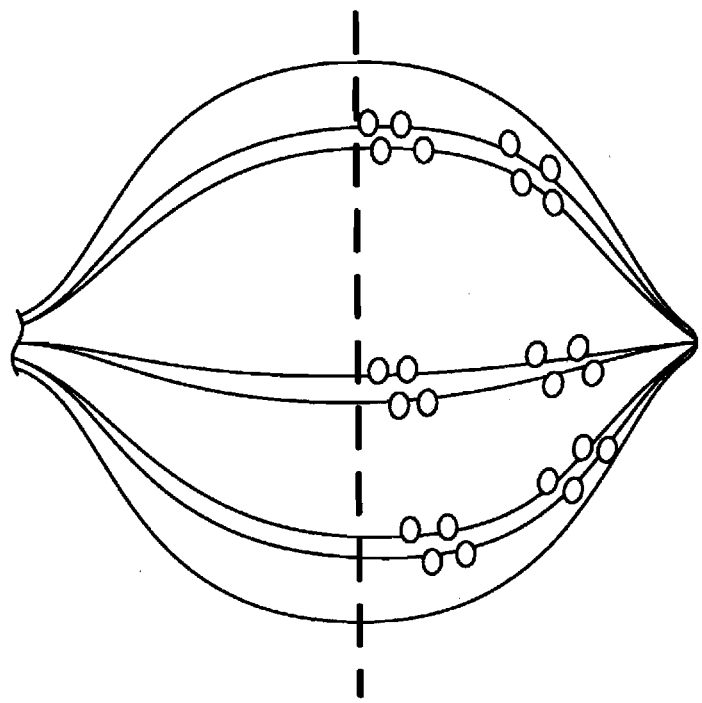
FIGS. 6A and 6B illustrate another example configuration of electrodes on the surface of the inflatable balloon of FIG. 1.
Figure 6B:
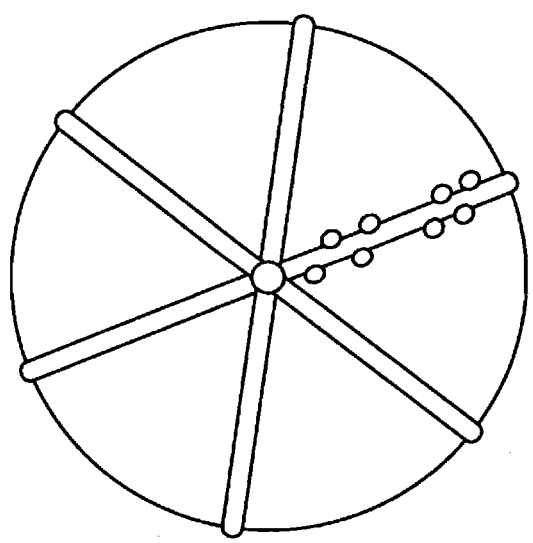

In some implementations, electrodes are disposed on the surface of the balloon portion 103 of the catheter, but they may be distributed differently than as depicted in the examples of FIG. 3 and FIG. 4. In particular, for example, as shown in FIG. 6A, the electrodes may be disposed primarily in the distal hemisphere of the balloon. Such an arrangement can be advantageous, since, in many implementations (such as those in which the ostium of a pulmonary vein or other body lumen or cavity is treated), only that portion of the balloon comes into contact with body tissue. In addition, with reference to FIGS. 6A and 6B, the electrodes may be staggered, rather than having a regular spacing along longitudinal lines. Such a staggered arrangement can be particularly advantageous with electrodes have a three-dimensional structure, to prevent the electrodes from bunching up when the balloon is in a collapsed arrangement (e.g., during insertion to and extraction from the treatment site).

Figure 7:
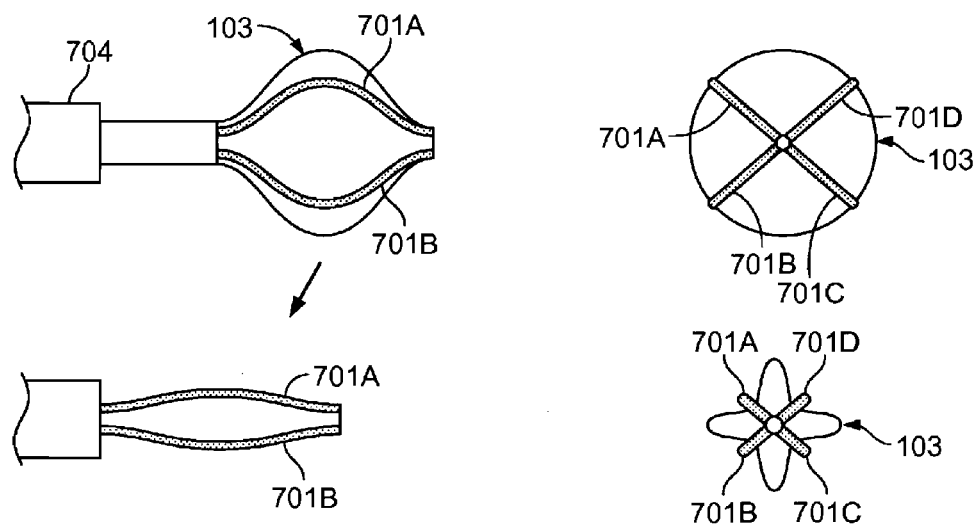
FIG. 7 illustrates example splines that can be employed in conjunction with the inflatable balloon of FIG. 1.

As described above, the electrodes are, in some implementations, disposed on splines. FIG. 7 and following illustrate various aspects of example splines 701A-D. As depicted in FIG. 7, the splines 701A-D can be a separate structure that surrounds the balloon portion 103 of the catheter. The splines 701A-D may or may not be attached to the surface of the balloon 103. (In FIG. 7, the splines are depicted as not being attached). When the balloon 103 is inflated, the splines 701A-D can conform to the shape of the balloon 103, and when the balloon 103 is deflated and withdrawn into an introducer sheath 704, the splines 701A-D can help deflate the balloon 103. In implementations in which the splines 701A-D are attached to one or more points on the surface of the balloon 103, the splines 701A-D may also help inflate the balloon 103. FIG. 7 illustrates four splines 701A-D, but as mentioned above, other numbers of splines are possible and contemplated.

The splines 701A-D can be constructed of various materials and have various shapes. For examples, splines can be made of Nitinol, spring steel, plastic, or some other polymer. The splines can have a round cross section (such as a wire), a rectangular cross section (such as a ribbon), or some other cross section, additional examples of which are illustrated in FIGS. 9A-9D. Moreover, the splines can be configured to have a particular shape when released (e.g., to help shape the balloon). For example, splines constructed from spring steel or a plastic with memory can have a natural bias in a shape that is therapeutically effective (e.g., a spherical "onion" shape; a slightly pointed "turnip" shape; a tapered "carrot" shape; a curved "banana" shape; or some other shape that useful in treating a particular part of the body). In some implementations, the splines can be biased inward, to assist in deflating the balloon, and the balloon itself can be constructed to have a particular therapeutically effective shape.

Figure 8:
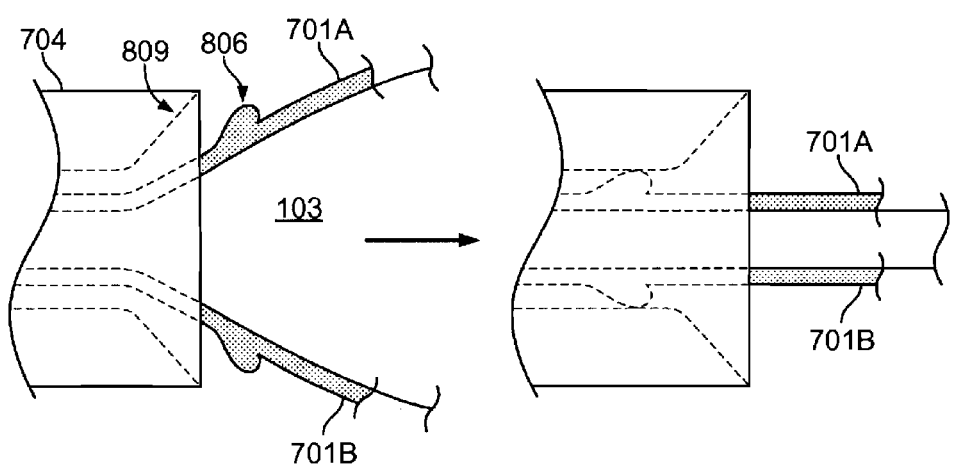
FIG. 8 illustrates an example structure on the splines shown in FIG. 7, which can be employed to help collapse the inflatable balloon.

FIG. 8 illustrates an additional structural feature that can be included in splines 701A and 701B to enable them to help deflate and collapse the balloon 103. In particular, the proximal edge of the spline 701A can include a ridge or protrusion 806 that cooperates with an angled surface 809 in an introducer sheath 704 of the catheter 100, such that as the balloon 103 is withdrawn into the introducer sheath 704, the angled surface 809 exerts additional force on the protrusion 806—and correspondingly, on the spline 701A—to help collapse the balloon 103. This is just one example structure, but the reader will appreciate that various other designs can be employed to exert pressure on the splines to enable them to more effectively deflate the balloon or prevent the balloon from bunching up or snagging as it is refracted into the sheath 704.

Figure 9A:
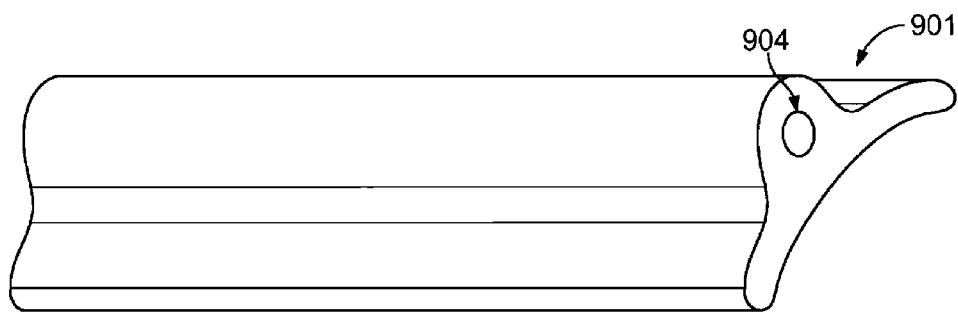
FIGS. 9A-9C illustrate example spline configurations.
Figure 9B:
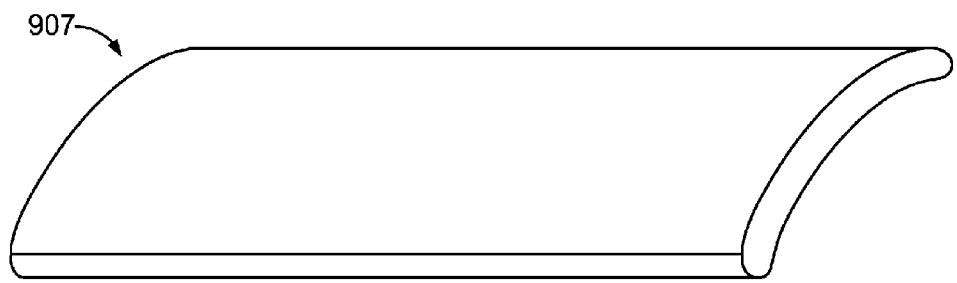
Figure 9C:
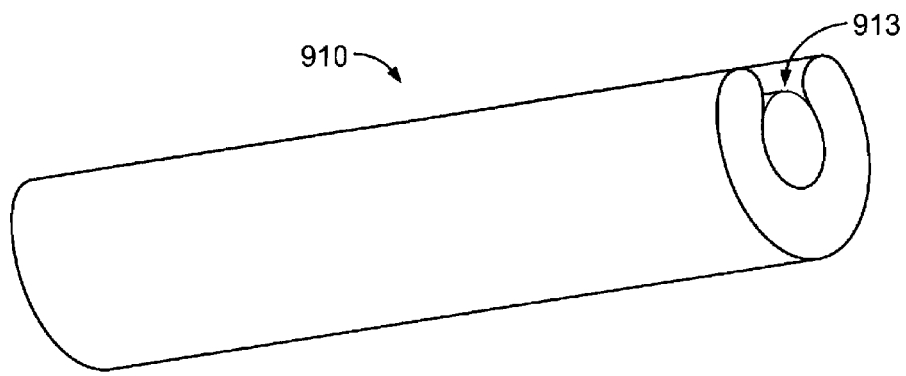

FIGS. 9A-9C illustrate various additional cross-sections of example splines. As shown in FIG. 9A, the spline 901 may have a ribbon shape with a channel 904 at the top for carrying wires to electrodes disposed on the spline (described in greater detail below), or for carrying a spring wire. In implementations that include a spring wire, the ribbon shape of the spline can distribute the pressure exerted by the spring wire across a larger area, which may minimize the risk of damage to the balloon. FIG. 9B illustrates an arc-shaped spline 907, that may provide greater strength in one particular direction (e.g., the arc may exert a greater force in the radial direction than other shapes). FIG. 9C illustrates an example spline 910 that is primarily circular in cross-section with a groove 913 (e.g., to carry wires for electrodes disposed on the spline and/or a spring wire).

Figure 10:
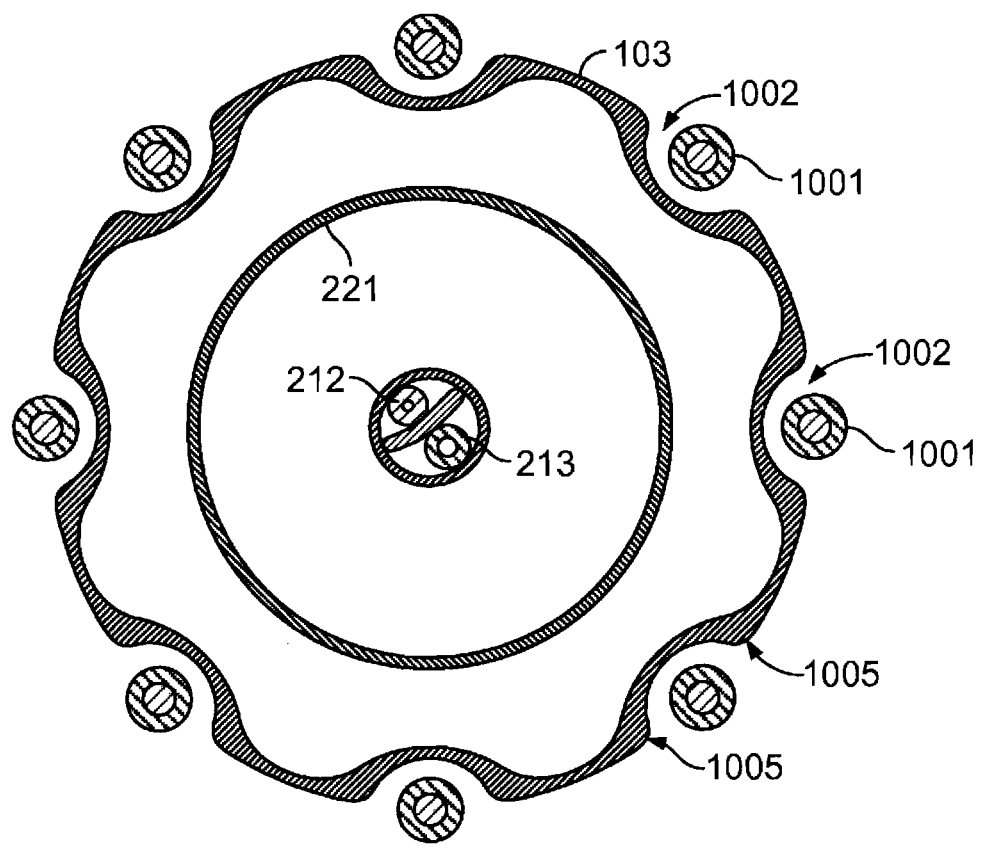
FIG. 10 is an example cross-section of the inflatable balloon portion shown in FIGS. 1 and 3.

As described above, the splines can be disposed around and adjacent to the balloon. In other implementations, splines may be more integral to the balloon 103, such as the example splines 1001. For example, with reference to FIG. 10—a cross section along lines D-D of the balloon 103 that is shown in FIG. 3—the outer balloon 103 may be constructed to have ridges or grooves 1002 that accommodate the splines 1001. In some implementations, the balloon material is thicker near the ridges or grooves, as depicted by the regions 1005. The regions 1005 of thicker balloon material may provide the spline functionality themselves, without an external, rigid spline structure 1001; or, as shown, the regions 1005 can accommodate a separate spline 1001. In some implementations, a groove in each region of thicker material 1005 can accommodate electrodes and corresponding wires in place of, or in addition to, splines. Other example structures are shown for reference in FIG. 10, including, for example, the inner balloon 221, guidewire lumen 213 and coolant delivery lumen 212.

Figure 11A:
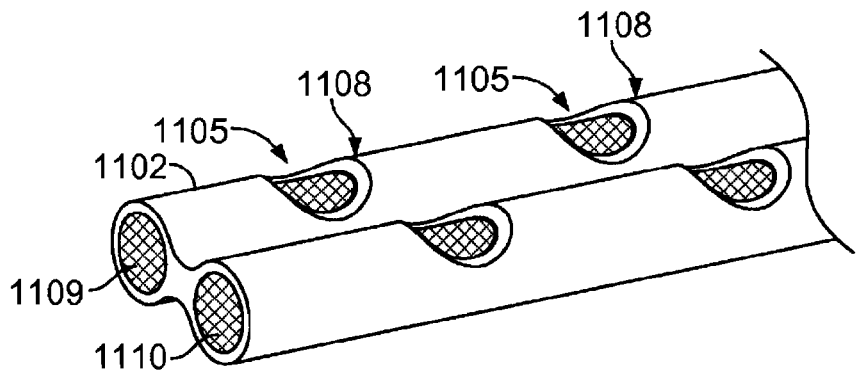
FIGS. 11A-11C illustrate example electrodes that can be included with the inflatable balloon of FIG. 1.

Various example electrodes and corresponding wiring schemes for the electrodes are now described with continued reference to the figures. FIG. 11A illustrates one example electrode construction in which electrodes are formed from insulated wire 1102 that is made from a biocompatible material (e.g., platinum-coated copper) by stripping the insulation away at appropriate points. In particular, for example, as shown in FIG. 11A, electrodes 1105 can be formed by stripping the insulation away at corresponding regions 1108. When the wires are in contact with body tissue, electrical contact can be made between the exposed wires at the regions 1108. In some implementations, the wires are, in size, on the order of 40 AWG (American wire gauge). FIG. 11A is merely exemplary, and other configurations are contemplated. For example, two conductors 1109 and 1110 are depicted in FIG. 11A, but a wire may have more conductors to provide a greater number of electrode contacts (e.g., four, six, eight, etc.). Moreover, the wires are shown as having a substantially circular cross-section and being individually insulated with substantially circumferential insulators, but other topologies are contemplated (e.g., rectangular or arc-shaped conductors that may provide spline functionality in addition to conducting electrical signals).

Figure 11B:
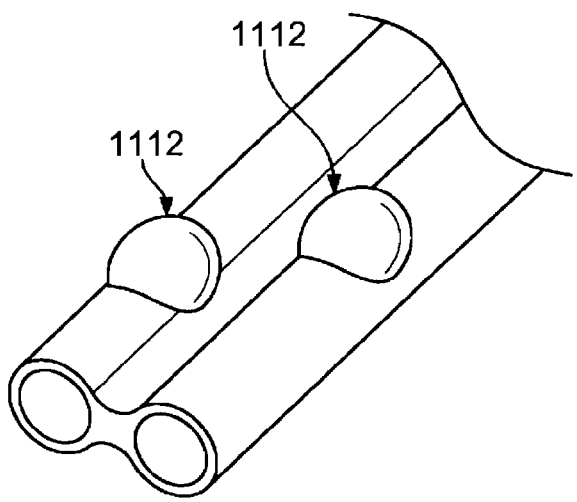

FIG. 11B illustrates another variation in which raised beads 1112 can be included to facilitate better contact between adjacent tissue (not shown) and exposed wires. As described above with reference to FIGS. 6A and 6B, and as depicted in FIG. 11B, the electrode beads 1112 can be staggered to prevent the electrodes from bunching up when the balloon on which they are disposed is collapsed. Staggering the electrodes as shown can also minimize the chance that adjacent electrodes will short together when the balloon 103 is deployed inside a patient.

Figure 11C:
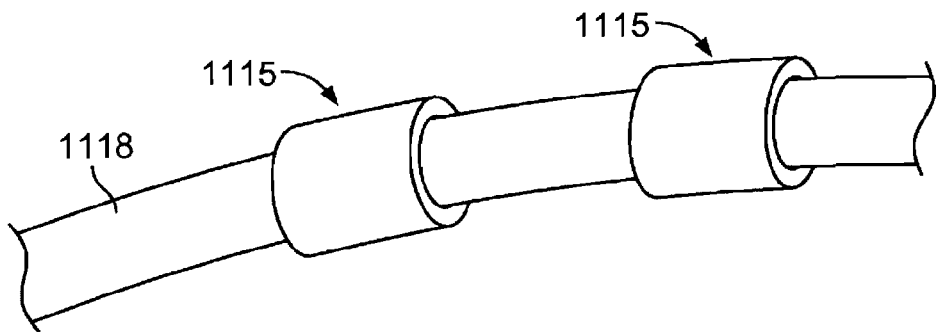

FIG. 11C illustrates another variation in which electrode rings 1115 can be included in the wires. In some implementations, electrode rings 1115 completely or substantially cover the circumference of a portion of a corresponding wire 1118, and can promote solid electrical contact between conductor(s) internal to the wire and adjacent tissue, regardless of the orientation of the wire when it is deployed with the balloon catheter.

Figure 12A:
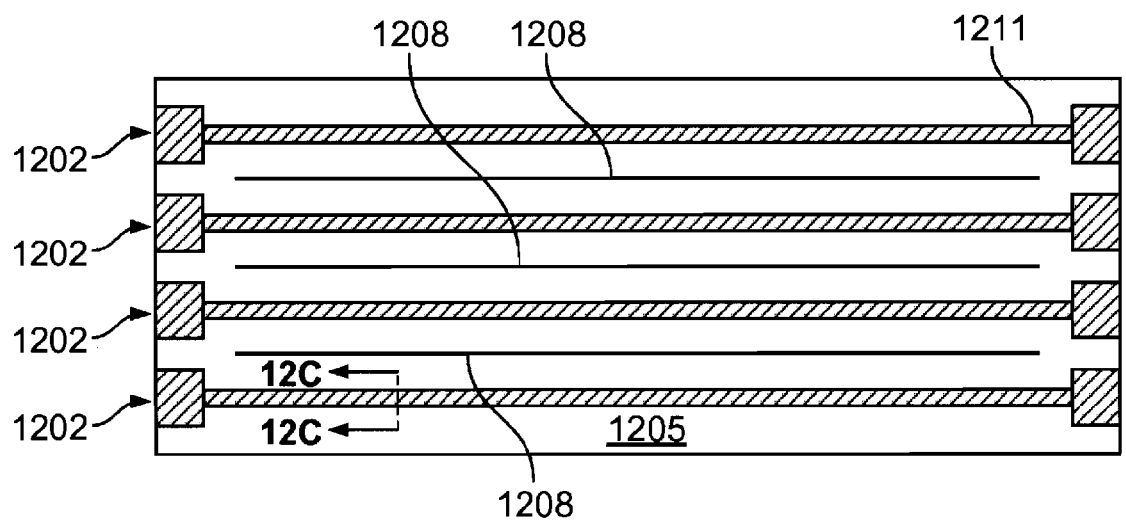
FIGS. 12A-12D illustrate another example spline and electrode structure.
Figure 12B:
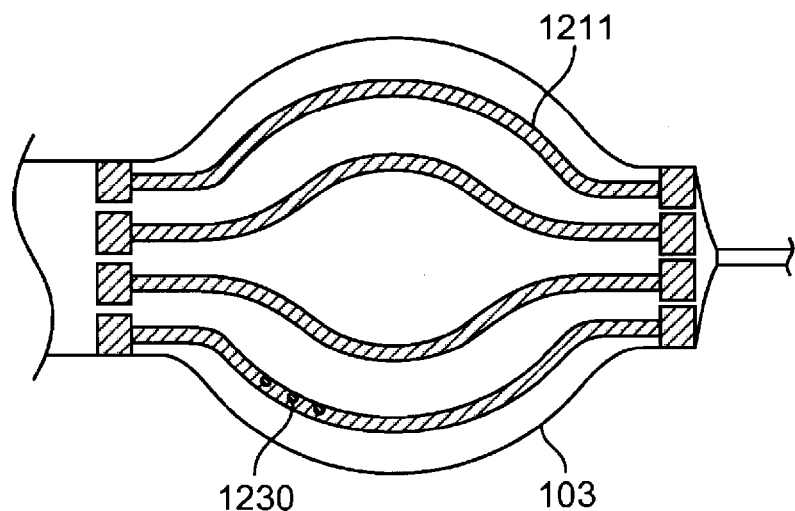

FIGS. 12A-12D illustrate another example spline and electrode structure. In particular, splines 1202 can be formed from a sheet 1205 of thin material, such as, for example, Kapton™. More particularly, slits 1208 can be made in the sheet 1205 of the material, such that the sheet 1205 can be formed into a cylinder or sphere and wrapped around and affixed to the outer surface a balloon 103, as depicted in FIG. 12B.

Figure 12C:
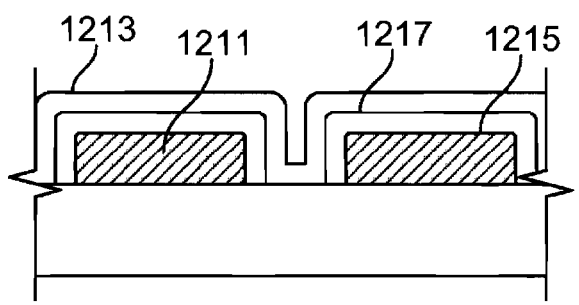

Electrical traces and electrodes can be formed on the flexible sheet 1205 of material as depicted in FIG. 12C. In particular, a conductor 1211 can be disposed on the flexible sheet 1205 of material and covered with insulation 1213, which can be selectively removed to form electrodes. For example, FIG. 12C illustrates two example traces disposed on the flexible sheet 1205 (e.g., Kapton™). As depicted, the traces include a layer 1215 of a first material (e.g., copper), which is coated by a layer 1217 of a second material (e.g., platinum), then covered with an insulator 1213. Two conductor layers may be advantageous in some implementations to promote strength, good electrical conductivity, and biocompatibility, and a copper-platinum combination may be particularly advantageous. Other implementations employ only a single conductor layer. To manufacture such electrodes and wires, the insulator 1213 can be selectively applied and removed, for example, using lithography and photo resists, or other appropriate techniques, as can the conductor layer(s) themselves.

Figure 12D:
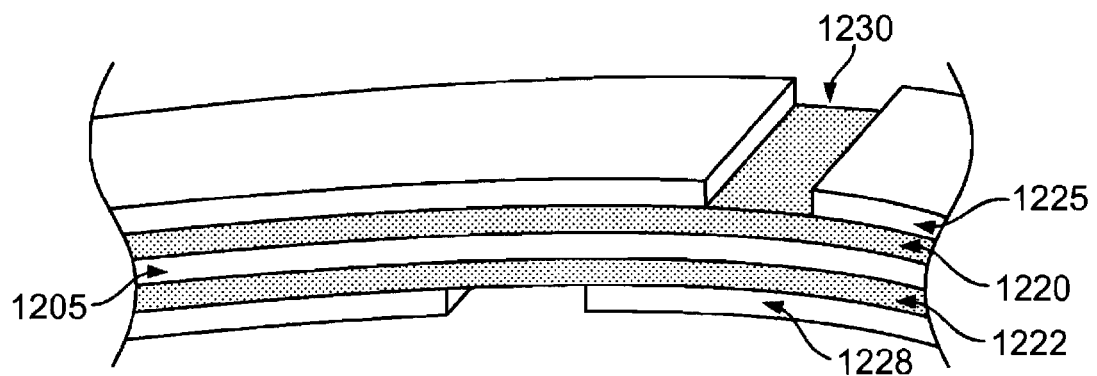

FIG. 12D illustrates an example cut-away view of a two-layer trace/electrode structure in which conductor layers 1220 and 1222 are disposed on both sides of the flexible sheet 1205 and selectively insulated with insulator layers 1225 and 1228 that is not applied in a region 1230 to form an electrode. In a two-layer implementation, a connection can be made through an opening (not shown) in the flexible sheet 1205 in order to connect conductors on one layer to conductors on the other layer, much like an electrical through-connection (e.g., a via) on a printed circuit board. Two-layer implementations may be advantageous where there are large number of electrodes, in order to dispose the electrodes on the layer of the flexible sheet 1205 that comes into contact with body tissue and to run signal paths to each electrode on the opposite side of the flexible sheet, where the signal paths may be more protected and less prone to break or become electrically open.

Figure 13:
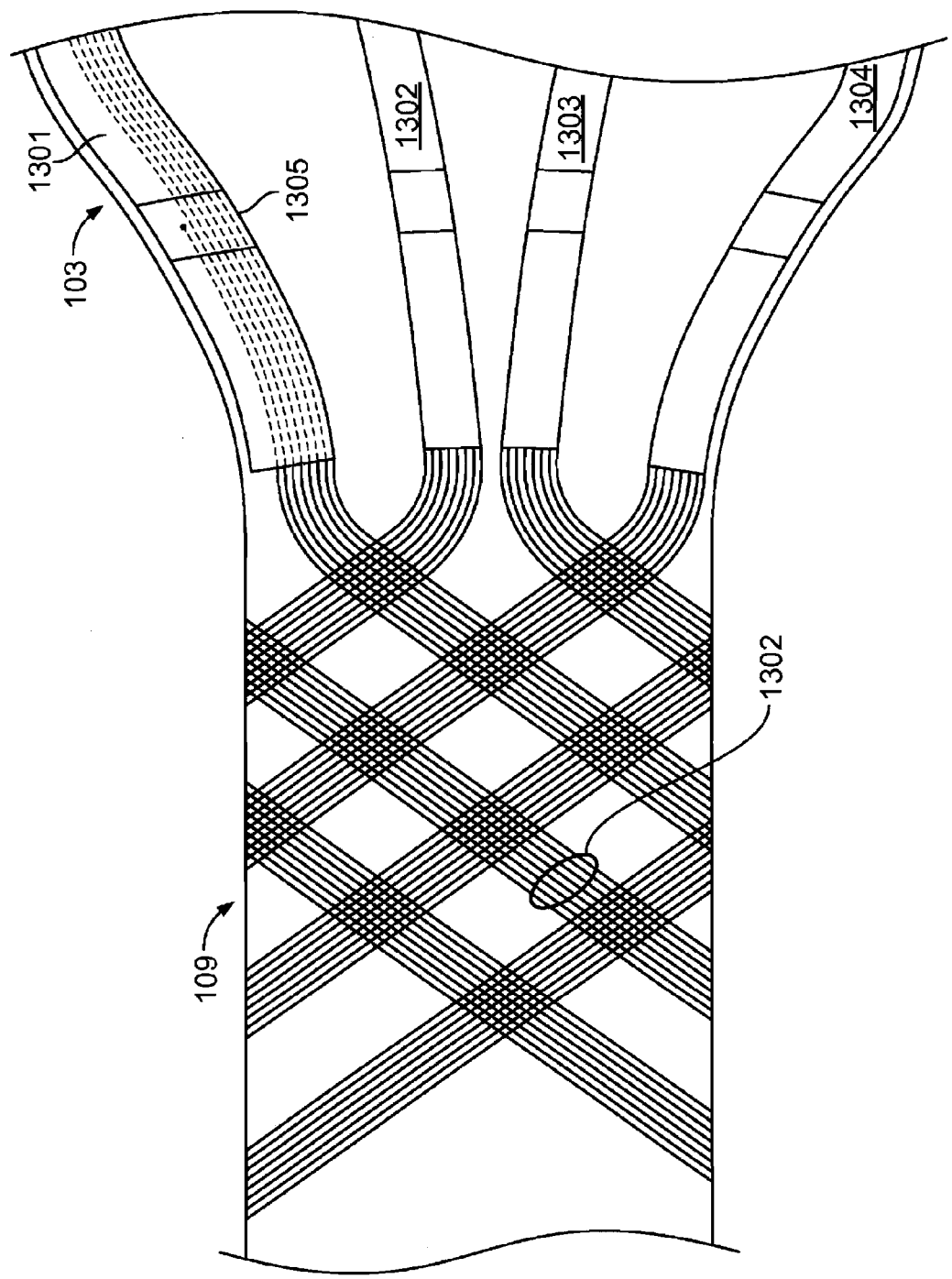
FIG. 13 illustrates an example wiring scheme for electrodes that can reinforce a shaft of the cryotherapy catheter shown in FIG. 1.

However the electrodes and wires are configured on the surface of the balloon 103, wires from the balloon can be routed to the proximal end of the catheter in various ways. For example, in some implementations, one or more dedicated lumens are employed to route individual electrode wires through the catheter shaft 109. In another implementation, as depicted in FIG. 13, wires 1302 may be used for a secondary purpose, such as strengthening the catheter shaft 109. In particular, for example, the wires can be embedded in the catheter shaft 109 in the form of a braid, as shown. At the distal end of the catheter shaft 109, individual wires from the braid can be separated out and routed to appropriate electrodes (e.g., electrode 1305) on different splines (e.g., splines 1301-1304).

Figure 14:
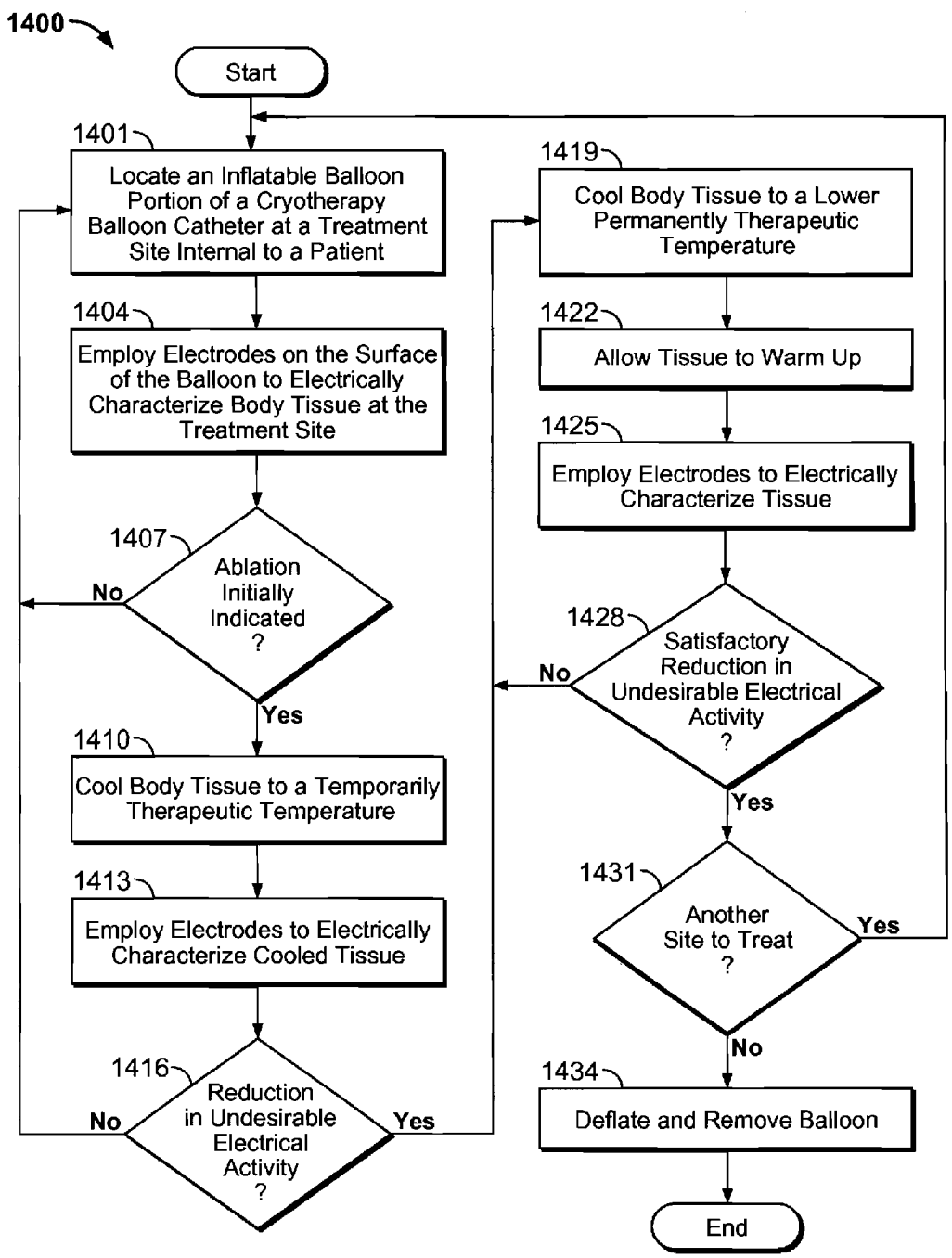
FIG. 14 is flow diagram of an example method of treating body tissue with the cryotherapy catheter shown in FIG. 1.

FIG. 14 is flow diagram of an example method 1400 of ablating body tissue with the cryotherapy catheter 100 that is described above. The inflatable balloon portion 103 can be located (1401) at a treatment site internal to a patient. For example, the distal balloon portion 103 can be disposed in a patient's left atrium in order to treat, with cryotherapy, atrial fibrillation resulting from aberrant electrical pathways in the patient's pulmonary veins. More particularly, the balloon 103 can be disposed in the ostium 402 one of the patient's pulmonary veins, as depicted in FIG. 4.

Electrodes on the surface of the balloon 103 can be employed to electrically characterize (1404) body tissue at the treatment site. For example, the electrodes 112 (and more particularly, the electrodes E1-E8 on each of splines A-D shown in FIG. 4) can be sampled by the signal processor 127 (see FIG. 1). The signal processor can analyze sampled biopotential values from the electrodes and provide output that enables a medical professional to, for example, identify aberrant electrical pathways in body tissue at the treatment site. The output can include, for example, graphical representations of the biopotential values at different points in time and presented in a manner that illustrates spatial relationship between different biopotential values, as depicted in FIGS. 5A-5D.

If the electrical characterization at action 1404 indicates that the body tissue being characterized is a candidate for ablation (decision box 1407), the tissue can be cooled (1410) to a temporarily therapeutic value (e.g., to a particular temperature, such as 0° C., or for a particular duration of time, such as 30 seconds or one minute). If the tissue is not a candidate for ablation, the inflatable balloon 103 can be repositioned at another region of tissue. Tissue (e.g., pulmonary vein tissue) may be a candidate for ablation when it unexpectedly propagates or generates electrical signals. More particularly, for example, tissue having an electrical characterization like that shown in FIG. 5A, 5B or 5C may be a candidate for ablation when an electrical characterization like that shown in FIG. 5D is expected. Cooling to a temporarily therapeutic value can include cryomapping the tissue (e.g., only mildly cooling or freezing the tissue, rather than freezing the tissue to a very low temperature). With reference to the overall cryotherapy catheter 100, cryomapping the tissue can include delivering an amount of cryogenic fluid to the chamber 215 of the inflatable balloon 103 (and exhausting an appropriate amount of the resulting gas) that results in the surface 118 of the balloon reaching a temperature appropriate for cryomapping, for an appropriate duration of time.

Once the tissue is cooled to a temporary therapeutic temperature, the tissue can again be electrically characterized (1413), as described above. If a reduction in undesirable electrical activity is observed (decision box 1416), the body tissue can be cooled (1419) to a lower, permanently therapeutic temperature. For example, if the initial electrical characterization of a particular region of body tissue is as shown in FIG. 5A, and electrical characterization of the temporarily cooled tissue is as shown in FIG. 5D, the temporary cooling may reveal that permanent ablation of the tissue is appropriate. In such a case, an additional volume of cryogenic fluid, for an additional time, can be delivered to the chamber 215, in order to cryo ablate the tissue. On the other hand, an unchanged electrical characterization of a particular regions of tissue (e.g., an electrical characterization as shown in FIG. 5 A, both before and after temporary cooling of the tissue) may indicate that the tissue being characterized is not the source of the undesirable electrical activity, and it may be more appropriate to reposition (1401) the inflatable balloon 103 at another region of tissue.

When tissue is treated, a sufficient volume of cryogenic fluid can be applied for a sufficient time to, for example, cool tissue to −20° C. or cooler, at a therapeutic depth (e.g., the thickness of the vessel or structure being treated, which in some cases may be 1-5 mm). In some implementations, appropriate cooling can be applied by delivering enough cryogenic fluid to the balloon to cool the external surface of the balloon to −60° to −90° C. for a period of time in the range of one to ten minutes. These values are exemplary, and the reader will appreciate that the volume of cryogenic fluid delivered and the time of delivery can be selected to achieve appropriate therapy goals in view of characteristics of the body tissue being treated.

Once treated, tissue can again be electrically characterized (1425), after it has warmed up (1422) enough to permit accurate characterization. In some implementations, the tissue is allowed to warm up to its nominal temperature (e.g., 37° C. for a human patient); in other implementations, the tissue may be characterized after it reaches a temperature that is higher than a cryomapping temperature, but before it reaches its nominal value. In some implementations, the flow of cryogenic fluid to the inflatable balloon 103 is stopped (or reduced to a rate that allows the balloon 103 to remain inflated but does not extract heat from the adjacent tissue), and the tissue is allowed to warm up on its own (e.g., through metabolism in cells of the treated tissue or tissue that is in thermal contact with the heated tissue, conduction of heat from tissue or blood that is in thermal contact with the treated tissue, etc.). In other implementations, a warming fluid (e.g., warm saline) may be injected into the balloon 103 to accelerate the warming process (1422).

If a reduction in undesirable electrical activity is observed (decision box 1428) following permanent treatment (1419) of the tissue, the balloon 103 can be repositioned (1401) at another treatment site, if one exists (decision box 1431); or the balloon 103 can be deflated and removed (1434) from the patient. If, on the other hand, an insufficient reduction in undesirable electrical activity is observed (decision box 1428), the cooling process 1419 can be repeated. In some implementations, even if the electrical characterization 1425 indicates a satisfactory reduction in undesirable electrical activity, the cooling process may be repeated a second time to increase the chances that the procedure will be effective over a long period of time.

The method 1400 is described above and in this document with primary reference to treating tissue of pulmonary veins of a patient in order to treat atrial fibrillation; however, the method can be employed in other regions of a patient to treat any other conditions, such as other conditions that benefit from cryotherapy and that may further benefit from electrical characterization of the tissue to be treated by the cryotherapy. Variations of the method 1400 are contemplated. For example, in some cases, actions in the method 1400 may be skipped or performed in a different order. In particular, for example, tissue may be immediately ablated by being cooled to a permanently therapeutic temperature, without intermediate actions and decisions 1410, 1413 and 1416 being performed. Moreover, tissue may be electrically characterized while it is being cooled, rather than in sequence with the cooling, or characterized at times other than those depicted in FIG. 14. Other variations are possible.

A number of implementations have been described. Nevertheless, it will be understood that various modifications may be made without departing from the spirit and scope of this document. Accordingly, other implementations are within the scope of the following claims.

What is claimed is:
1. A device, comprising:
a catheter extending along a longitudinal axis;
a balloon coupled to an end of the catheter; and
a plurality of separate flexible electrode assemblies circumferentially spaced apart from each other and attached to an outer surface of the balloon, each electrode assembly comprising a polymeric substrate, a plurality of conductive members extending longitudinally along an outer surface of the polymeric substrate, and an insulator disposed over at least a portion of each of the conductive members;

wherein at least one of the flexible electrode assemblies include a distal electrode and a separate proximal electrode that are spaced apart longitudinally from each other and are defined along at least one of the conductive members, defined along at least one of the conductive members.

2. The device of claim 1, further comprising at least one heat sensing device.

3. A device, comprising:
an elongated catheter;
an expandable balloon associated with the catheter; and
a plurality of circumferentially spaced flexible circuits extending longitudinally along a surface of the expandable balloon, the flexible circuits spaced apart from each other such that regions of the balloon are viewable between the flexible circuits, each flexible circuit including a polymeric substrate, a plurality of conductive members extending longitudinally along an outer surface of the polymeric substrate, and an insulator disposed over at least a portion of each of the conductive members;

wherein each flexible circuit includes at least a distal electrode and a separate proximal electrode, wherein the distal electrode and the proximal electrode are spaced apart axially and circumferentially relative to each other, wherein the flexible circuits are secured to the expandable balloon.

4. The device of claim 3, wherein each flexible circuit includes at least one opening extending completely through the flexible circuit.

5. The device of claim 3, wherein the distal and proximal electrodes are separated by an intermediate element.

6. A medical device, comprising:
a catheter shaft having a distal region;
an expandable balloon attached to the distal region;
a plurality of flexible circuits coupled to the expandable balloon;
wherein each of the flexible circuits includes a polymeric substrate secured to an outer surface of the balloon, a conductive member extending longitudinally along the polymeric substrate, and an insulator disposed along the conductive member, wherein the plurality of flexible circuits are separate elements, spaced circumferentially from each other; and
wherein a proximal electrode and a distal electrode are defined at separate locations spaced apart longitudinally along at least one of the plurality of flexible circuits at regions of the conductive member where the insulator is absent.

7. The medical device of claim 6, wherein the polymeric substrate includes a polymeric sheet that is wrapped about the expandable balloon.

8. The medical device of claim 6, wherein the polymeric substrate includes a polyimide.

9. The medical device of claim 6, wherein the conductive member includes copper.

10. The medical device of claim 6, wherein the conductive member includes two layers.

11. The medical device of claim 10, wherein the conductive member includes a layer of copper and a layer of platinum.

* * * * *